United States Patent

Mahood

Patent Number: 5,543,102

Date of Patent: Aug. 6, 1996

[54] MELT EXTRUSION PROCESS

[75] Inventor: James A. Mahood, Morgantown, W. Va.

[73] Assignee: General Electric Company, Pittsfield, Mass.

[21] Appl. No.: 361,259

[22] Filed: Dec. 21, 1994

Related U.S. Application Data

[63] Continuation-in-part of Ser. No. 307,545, Sep. 16, 1994, Pat. No. 5,424,348, which is a continuation of Ser. No. 96,530, Jul. 22, 1993, abandoned.

[51] Int. Cl.$^6$ .................................................. D01F 1/02
[52] U.S. Cl. ........................................... 264/211; 524/117
[58] Field of Search ............................... 264/211; 524/117

[56] References Cited

U.S. PATENT DOCUMENTS

| | | |
|---|---|---|
| 2,604,667 | 7/1952 | Hebeler . |
| 2,957,757 | 10/1960 | Coates et al. . |
| 3,002,804 | 10/1961 | Kilian . |
| 3,039,993 | 6/1962 | Friedman . |
| 3,056,823 | 10/1962 | Hechenbleikner et al. . |
| 3,264,247 | 8/1966 | Freidman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Freidman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,771,307 | 11/1973 | Petrille . |
| 3,772,872 | 11/1973 | Piazza et al. . |
| 3,794,629 | 2/1974 | Eimers et al. . |
| 3,845,168 | 10/1974 | Guttag . |
| 4,086,304 | 4/1978 | Hutton et al. . |
| 4,134,882 | 1/1979 | Frankfort et al. . |
| 4,156,071 | 5/1979 | Knox . |
| 4,196,117 | 4/1980 | Spivack . |
| 4,302,383 | 11/1981 | Valdiserri et al. . |
| 4,305,866 | 12/1981 | York et al. . |
| 4,318,845 | 3/1982 | Spivack et al. . |
| 4,403,053 | 9/1982 | Lewis . |
| 4,405,739 | 9/1983 | Kinson . |
| 4,413,078 | 11/1983 | Lewis et al. . |
| 4,529,533 | 7/1985 | Chasar . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,956,406 | 9/1990 | Myers et al. . |
| 4,957,954 | 9/1990 | Iizuka et al. . |
| 4,994,529 | 2/1991 | Sekiguchi et al. . |
| 4,997,888 | 3/1991 | Sekiguchi et al. . |

FOREIGN PATENT DOCUMENTS

| | | |
|---|---|---|
| 2944254 | 5/1980 | Germany . |
| 903427 | 8/1962 | United Kingdom . |
| 1487843 | 10/1977 | United Kingdom . |
| 1574305 | 9/1980 | United Kingdom . |
| 2087399 | 5/1982 | United Kingdom . |

Primary Examiner—Veronica P. Hoke

[57] ABSTRACT

Melt extrusion processes utilizing a neo alkyl phenyl phosphite stabilized polyolefin composition are provided. The processes exhibit reduced levels of screen pack plugging during fiber and film extrusion processes compared to processes utilizing various other phosphites.

12 Claims, 1 Drawing Sheet

MELT EXTRUSION PROCESS

This is a continuation-in-part of Ser. No. 08/307,545 filed Sep. 16, 1994, now U.S. Pat. No. 5,424,348 which in turn is a continuation of Ser. No. 08/096,530 filed Jul. 22, 1993, now abandoned.

BACKGROUND OF THE INVENTION

1. Field of the Invention

The present invention relates to a melt extrusion processes, and more particularly relates to melt extrusion processes for making polypropylene fibers or films.

BACKGROUND OF THE INVENTION

Processes for making polymeric fibers and films are known, see U.S. Patent Nos. Knox, U.S. Pat. No. 4,156,071, issued May 22, 1979, Frankfort et al, U.S. Pat. No. 4,134,882, issued Jan. 16, 1979, Piazza et al., U.S. Pat. No. 3,772,872, issued Nov. 20, 1973, Petrille, et al., U.S. 3,771,307, issued Nov. 13, 1973, Kilian, U.S. Pat. No. 3,002,804, issued Oct. 3, 1961, Coates et al., U.S. Pat. No. 2,957,747, issued Oct. 25, 1960, Hebeler, U.S. Pat. No. 2,604,667, issued Jul. 29, 1952, all of which are incorporated herein by reference, and Great Britain Patent Nos. 903427, published Aug. 15, 1962, 1487843, published Oct. 5, 1977 and 1574305, published Sep. 3, 1986, all of which are incorporated herein by reference. Phosphites are known stabilization additives for polyolefins, see York, U.S. Pat. No. 4,305,866, Lewis, U.S. Pat. No 4,403,053, issued Sep. 6, 1983 and Valdiserri et al, U.S. Pat. No. 4,302,383, issued Nov. 24, 1981, all of which are incorporated herein by reference.

Polyolefin processors are attempting to process polymer at increasing temperatures and with increased shear and work on the polymer. They are also processing polymer which may contain polymerization catalyst residues. The total residual metal content has been decreasing in recent years but the catalyst residue may still be active.

This combination of more abusive processing conditions and the possibility of catalyst residue still being active may lead to difficulties when trying to process the polymers.

Catalyst "neutralizers" are well known in the art and are generally used in most formulations to inhibit corrosion of processing equipment resulting from catalyst residues. Typical examples would be: Ca, Zn, or Mg Stearates, Ca, Zn, or Mg oxides and synthetic hydroltalcite compositions such as a product manufactured and sold by Kyowa as DHT4A.

In many of the high temperature melt processes such as fiber spinning and film manufacture, screen packs are utilized to remove small particles which may be in the polymer prior to the polymer passing through the small orifices used in fiber and film processes. With the higher processing temperature/high shear applications there is a tendency for some combinations of polymers and additive formulations to be prone to screen pack plugging.

Specifically, it has been discovered, however, that stabilized polyolefin compositions containing residual catalysts, can generate solid byproducts during melt extrusion processes. These solids must be filtered out from the melt stream.

For example, melt stream fiber forming processes and film forming processes or the fiber and/or film forming dies will become clogged or the final articles (films/fibers) will exhibit defects and blemishes. Too much solid generation will lead to frequent filter clogging, referred to as screen pack plugging, which leads to increased processing pressures and reduced process throughput.

Consequently, there is a need for improved polyolefin compositions and improved melt extrusion processes that will exhibit reduced solid byproduct formation and a resulting reduced filter clogging and a reduced increase in processing pressure and improve throughputs.

SUMMARY OF THE PRESENT INVENTION

Figure 1:
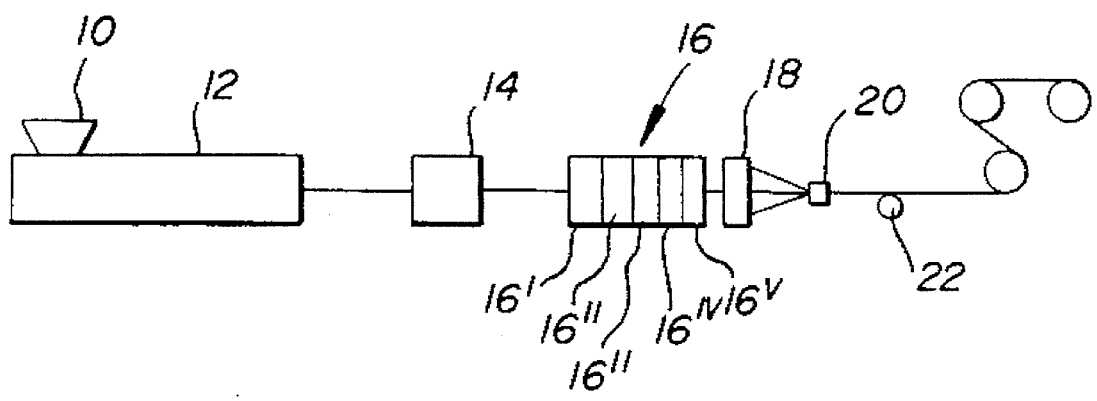
FIG. 1 is a schematic drawing of the process of the present invention for making fibers.

The present invention involves an improved polyolefin melt extrusion process that exhibits reduced filter clogging. The process involves (a) forming a polyolefin composition comprising a polyolefin resin, a phosphite stabilizer, and optionally a primary antioxidant, (b) melt extruding the composition through a filter to produce a filtered melt stream, and (c) passing the melt stream through a die to make the plastic article. The utilization of a particular neo alkyl phenyl phosphite surprisingly and unexpectedly results in a substantial reduction in filter clogging.

DETAILED DESCRIPTION OF THE INVENTION

The olefin polymers contemplated herein include homopolymers and copolymers of monoolefins, preferably those monoolefins containing 1–4 carbon atoms. Illustrative examples include polyethylene (including low density, high density, ultra high molecular weight and linear low density polyethylene), polypropylene, EPDM polymers, ethylene-propylene copolymers and polyisobutylene. The stabilization of mixtures of any of these olefin polymers and copolymers likewise is contemplated.

Any polypropylene resin melt extrusion process involving polymer filtration can be improved by the process of the present invention, including propylene homopolymers and random or block copolymers of propylene and an α-olefin which contain ethylene or other α-olefin in an amount from 1 to 30 wt. % as well as blends of polypropylene with other olefin polymers and copolymers, such as low and high density polyethylene, ethylene/vinyl acetate copolymer, ethylene/propylene copolymer rubbers and styrene/butadiene block-copolymer rubbers.

The present invention involves a neoalkyl aryl phosphite of the formula:

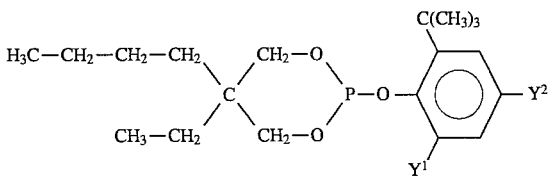

wherein $Y^1$ is independently selected from the group consisting of alkyl radicals, and preferably $Y^1$ is a tert-butyl group and $Y^2$ is a tert-butyl or sec-butyl group.

The phosphite may be made by the reaction of 2-ethyl-2-butyl-1,3-propane diol with $PCl_3$ in the absence of a catalyst, HCl acceptor and solvent to produce an intermediate product of the formula:

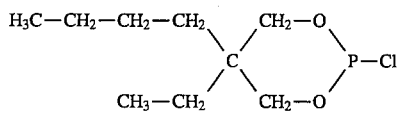

followed by the reaction with a hydroxyaryl compound of the formula:

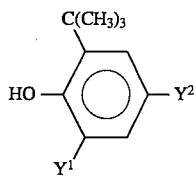

wherein $Y^1$ and $Y^2$ are as defined above. Suitable reaction methods are set out in Great Britain Patent 2087399A, U.S. Patent Spivak et al. U.S. Pat. No. 4,318,845 issued 1982, and Article in Phosphourous & Sulfur Journal by J. D. Spivak et al. 1983, vol. 15, pp. 9–13, all of which are incorporated herein by reference.

The reaction between the diol and $PCl_3$ may be conducted in known manner, as by mixing the reactants together at room temperature, or preferably, by cooling the $PCl_3$ to a temperature between 5–15 degrees centigrade prior to addition of diol to the reactor. An excess of either reactant may be employed although it is preferred to operate with substantially stoichiometric amounts of the diol and $PCl_3$. The reaction temperature is preferably maintained between 5–15 degrees centigrade. This temperature may be readily controlled by regulating the rate of diol addition. The esterification reaction is quite exothermic in the absence of a solvent, but a temperature moderating effect is produced by the cooling effect of vigorous HCl evolution. Hence, by effective control of diol addition, the reaction may be made self-regulating in the temperature range between 5–15 degrees centigrade.

After the reaction has gone to completion, the bulk of the by-product HCl may optionally be removed by gently raising the temperature of the product to about 50 degrees centigrade and applying a vacuum.

The reaction between the intermediate product of the reaction discussed in the preceding paragraph and hydroxyaryl compound may be conducted in the same reaction vessel that was employed to produce the crude intermediate by merely introducing the hydroxyaryl compound into the reactor.

The reaction between the hydroxyaryl compound and the intermediate product in some instances may be carried out at a temperature between 35 to 100 degrees centigrade and preferably between about 45 to about 80 degrees centigrade. The pressure of the reaction system is maintained between about 50 millimeters mercury absolute to atmospheric pressure. The reaction reaches substantial completion in from 1 to about 8 hours and for practical purposes it is preferably operated under temperature and pressure conditions which will afford the maximum amount of product within 3 to about 5 hours. Although a stoichiometric excess of either reactant may be employed, it is preferred to operate with substantially stoichiometric quantities.

The hydroxyaryl compound may be any compound of the formula:

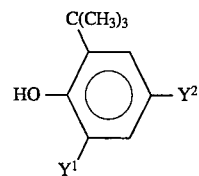

in which $Y^1$ is selected from the group consisting of alkyl groups preferably having from 1 to 8 carbon atoms, more preferably methyl or t-butyl. The reaction can be completed in the presence of a base such as an amine acceptor. Since $Y^1$ is an alkyl group, an amine acceptor should be added to help drive this reaction. If $Y^1$ is a tert-alkyl group, such as t-butyl, then a stociometeric amount of amine acceptor should be present. $Y^2$ is selected from sec-butyl and t-butyl groups. If $Y^2$ is a t-butyl group then the phosphite is a solid at room temperature. Preferably $Y^2$ is sec-butyl so that the phosphite is a liquid at room temperature.

After completion or near completion of the reaction, HCl generated during the process may readily be substantially removed by evacuating the reactor vessel. No special precautions need to be taken to remove all the HCl present, as by addition of HCl acceptor or via controlled neutralization of the acidity. The product may then be recovered by distillation, or crystallization.

The phosphites have $Y^1$ as an alkyl group such as methyl or t-butyl in order to inhibit ultraviolet light yellowing of the phosphite. If $Y^1$ is hydrogen the phosphite will have sensitivity to UV yellowing. The preferred phosphite has a phenolic degradation product boiling point of greater than 250° C., more preferably greater than 260° C. so that the volatility of the degradation product during processing of the stabilized polymer, such as polyolefins such as polypropylene which processes at 240° C. and above, is minimized. The problem of excessive volatiles can be minimized by employing an 2,4-di-t-butyl-6-alkyl phenyl group because such groups have corresponding 2,4-di-t-butyl-6-alkyl phenol degradation products which have a boiling point of greater than 260° C.

The present invention also is a stabilized polymer composition which includes an effective amount of one or more of the phosphites described above. An amount of the phosphites of the invention is considered to be an "effective amount" when the polymer composition containing the phosphites of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more.

The resulting stabilized polymer compositions of the invention may optionally also contain (or be free of) various conventional additives, such as the following:

1. Antioxidants 1.1 Alkylated monophenols, for example: 2,6-di-tertbutyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alpha-methylcyclohexyl)-4,6 dimethylphenol, 2,6-di-octadecyl-4-methylphenol, 2,4,6,-tricyclohexyphenol, 2,6-di-tert-butyl-4-methoxymethylphenol.

1.2 Alkylated hydroquinones, for example, 2,6-di-tert-butyl-4-methoxyphenol, 2,5-di-tert-butyl hydroquinone, 2,5-di-tert-amyl-hydroquinone, 2,6-diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'- methylene-bis-(4-methyl-6-(alpha-methylcyclohexyl(phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(alpha-methylbenzyl)- 4-nonylphenol), 2,2'-methylene-bis-(6-(alpha,alpha-dimethylbenzyl)- 4-nonyl-phenol). 2,2'-methylene-bis-( 4,6-di-tert-butylphenol), 2,2'-ethylidene-bis-( 6-tert-butyl-4 -isobutylphenol), 4,4'-methylene-bis-( 2,6-di-tert-butylphenol), 4,4'- methylene-bis-( 6-tert-butyl-2-methylphenol), 1,1-bis- (5-tert-butyl-4-hydroxy-2-methylphenol)butane. 2,6- di-(3-tert-butyl-5-methyl-2-hydroxybenzyl)-4methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-( 3-tert-butyl-4-hydroxy- 5-methylphenyl)-dicyclopentadiene, di-(2-(3'-tert-butyl- 2'-hydroxy-5'-methyl-benzyl)-6-tert-butyl-4-methylphenyl)terephthalate.

1.5 Benzyl compounds, for example, 1,3,5-tris-( 3,5-di-tert-butyl-4-hydroxybenzyl)-2,4,6-trimethylbenzene, bis-(3, 5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris-(3,5-dicyclohexyl- 4-hydroxybenzyl)isocyanurate.

1.6 Acylaminophenols, for example, 4-hydroxy-lauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl-4-hydroxyphenyl)-carbamate.

1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethylisocyanurate, thiodiethyleneglycol, dihydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.9 Esters of beta-(5-tert-butyl-4-hydroxy-3-methylphenyl)propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl)isocyanurate, thiodiethylene glycol, N,N-bis(hydroxyethyl)oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)-hexamethylen-diamine, N,N'-di-(3, 5-di-tert-butyl-4-hydroxyphenylpropionyl)trimethylenediamine, N,N'-di-(3, 5-di-tert-butyl-4-hydroxyphenylpropionyl)hydrazine.

2. UV absorbers and light stabilizers.

2.1 2-(2'-hydroxyphenyl)-benzotriazoles, for example, the 5'methyl-, 3'5'-di-tert-butyl-, 5'-tert-butyl-, 5'( 1,1,3,3-tetramethylbutyl)-, 5-chloro-3',5'-di-tert-butyl-, 5-chloro-3'tert-butyl-5'-methyl-, 3'sec-butyl-5'tert-butyl-, 4'-octoxy, 3',5'-ditert-amyl-3',5'-bis-(alpha,alpha-dimethylbenzyl)-derivatives.

2.2 2-Hydroxy-benzophenones, for example, the 4-hydroxy-4-methoxy-, 4-octoxy, 4-decloxy-, 4-dodecyloxy-, 4-benzyloxy, 4,2',4'-trihydroxy- and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methylindoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)piperdine; and N-(1-hydroxy-2,2,6,6-tetramethyl-piperidin-4-yl)-epsiloncaprolactam.

2.7 Oxalic acid diamides, for examples, 4,4'-dioctyloxyoxanilide, 2,2'-di-octyloxy-5',5'-di-tertbutyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1, 2,4-triazole, bis-benzyliden-oxalic acid dihydrazide.

4. Phosphites and phosphonites, for example, triphenyl phosphite, diphenylalkyl phosphites, phenyldialkyl phosphites, tris (nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tertbutylphenyl)pentaerythritol diphosphite tristearyl sorbitol triphosphite, and tetrakis(2,4-di-tert-butylphenyl)4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate.

8. Nucleating agents, for example, 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate;ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, epoxidized vegetable oils, such as epoxidized soybean oils, lubricants, emulsifiers, pigments, hydroxylamines, such as $R_2NOH$ wherein R is a $C_1$ to $C_{30}$ alkyl group, such as propyl or stearyl, optical brighteners, flameproofing agents, anti-static agents, blowing agents and thiosynergists such as dilaurythiodipropionate or distearylthiodipropionate. Optionally, the polymer compositions are free of the above additives.

Olefin polymers may be produced by polymerization of olefins in the presence of Ziegler-Natta catalysts optionally on supports such as but not limited to $MgCl_2$, chromium salts and complexes thereof, optionally supported on Silica or other materials. They may also be produced utilizing catalysts based on cyclopentadiene complexes of metals typically complexes of Ti and Zr. It is believed that residual amounts of catalyst, for example 1 part per million (ppm) by weight based on the total weight of polymer to 100 ppm, contributed to undesirable screen pack plugging in various polyolefin melt extrusion processes. Utilization of the present neo alkyl phenyl phosphites substantially reduces undesirable screen pack plugging in polyolefin melt extrusion processes.

The polyolefin resin compositions preferably comprise from 50 to 99.9 weight percent polyolefin resin, more preferably from 90 to 99.5 weight percent thereof, and most preferably from 95 to 99 weight percent thereof based on the total weight of the composition; from 0.01 to 5 weight percent phosphite, more preferably from 0.05 to 3 weight percent thereof, and most preferably from 0.1 to 1 weight percent thereof based on the total weight of the composition.

Polyolefin fibers are typically made by melt spinning processes. Melt spinning requires that the polyolefin polymers be stable at temperatures sufficiently above the melting point or softening point of the polyolefin to be extruded in the molten state without substantial degradation. The melt spinning process employs a spinneret, which is a plate containing orifices through which molten polymer is extruded under pressure. Typically the spinneret is made of stainless steel or a nickel alloy. The spinneret is a flat plat, flush with or recessed in its mounting. Spinnerets for molten polymers are usually from 3 mm to 10 mm thick, for melt process pressures of up to 3000 psi. Fibers forming spinneret holes may have exit diameters of from 175 to 750 microns. The number of holes in the spinneret may range from a few to several thousand. A typical process is shown schematically in FIG. 1, wherein the polyolefin composition in particulate form is fed via a hopper 10 to a screw type extruder 12 wherein the composition is melted at elevated temperatures to form a melt stream which is forced at elevated pressures to a metering pump 14 which controls the flow. Optionally, there may be a filtration unit (not shown) at the exit of the extruder 12. The melt stream is then forced through a filter 16, preferably a screen pack filter of filters in series ($16^i$, $16^{ii}$, $16^{iii}$, $16^{iv}$, $16^v$) with the upstream filters being of a mesh for collecting only large particles and subsequent downstream filters being increasingly fine for collecting smaller particles that pass through the upstream filters, which removes unmelted solids prior to the melt stream reaching the spinneret 18. The filtered use of stream is then forced to the spinneret 18 wherein fibers are formed by passing the melt stream through the die holes of the spinneret. The fibers are then air cooled and converged into the convergence guide 20, then directed to the finish application 22, reels 24, 26, and finally to the spin bobbin 28 wherein the fiber is wound for storage.

Before reaching the spinneret, the molten polymer is filtered through a series of sintered or fibrous metal gauzes or a bed of graded fine refractory material, such as sand or alumina, held in place by metal screens. Filtration removes large solid or gel particles that might otherwise block spinneret holes or, if passed through, occupy sufficient cross-sectional area in the filament to affect its processing or tensile properties. Smaller particles, such as delusterants, are not retained by the filter. Filtration also provides shearing, and thus can influence rheological behavior.

Figure 2:
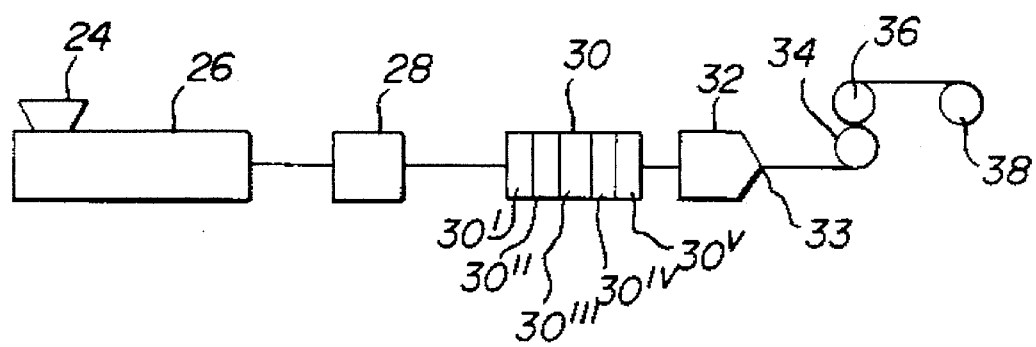
FIG. 2 is a schematic drawing of the process of the present invention for making films.

As shown in FIG. 2, a film making process may involve feeding polyolefin particulates (pellets or powder) to a hopper 24 of a screw type extruder 26 wherein the particulates are melted and forced to a metering pump 28 (optional) and then forced through a filtering system (preferably a screen pack) 30 which preferably has a series of filters (30 $30^{iii}$, $30^{iv}$ and $30^v$) which have increasingly fines mesh as the polyolefic melt flows downstream. The filter screens out the unmelted solid by-products before the polyolefin melt stream reaches the die 32 so that the dies orifice 33 will not become clogged by the solid by-products. The melt stream flows from the filter system 30 to the die 32, through the elongated die orifice 33, forming a polyolefin film which then passed partially around and between calendar rolls 34, 36 to storage roll 38 whereupon the film is wound and stored.

The screen filter preferably has a mesh size of from 50 to 1000.

Examples

Comparative Example A was a polypropylene composition containing 500 ppm of Calcium Stearate, 500 ppm of bis(2,4-di-tert-butylphenyl)pentaerythritol diphosphite, 250 ppm of hindered phenolic compound (Irganox 3114).

Example 1 was a polypropylene composition containing 500 ppm of Calcium Stearate, 500 ppm of Phos 1, and 250 ppm of hindered phenolic compound (Irganox 3114). Phos 1:

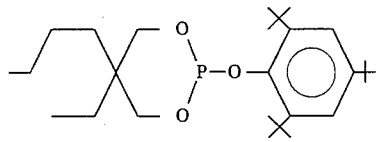

TABLE 1

| Examples | Ex 1 | CEXA |
|---|---|---|
| Back Pressure Increase (psi) | 0 (13 hrs) | 500 (8 hrs) |

Note that the example (EX 1) of the present invention exhibited no back pressure increase after 13 hours of operation whereas the comparative example (CEXA) exhibited a 500 psi increase in back pressure after only 8 hours.

What is claimed is:

1. An extrusion process for making plastic articles, said process comprising:
   a) forming a polyolefin composition comprising a polyolefin resin, and a thermal stabilizing amount of a phosphite of the formula:

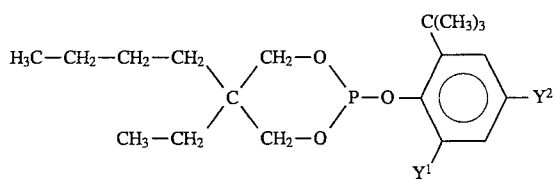

wherein $Y^1$ is an alkyl and $Y^2$ is selected from tert-butyl and sec-butyl,
   b) melt extruding said composition through a filtration system to produce a filtered polyolefin melt stream,
   c) passing said melt stream through a die to make the plastic article.

2. The process of claim 1 wherein $Y^1$ is methyl.

3. The process of claim 1 wherein $Y^1$ is a tert-butyl group.

4. The process of claim 1 wherein said polyolefin is polypropylene.

5. The process of claim 3 wherein said polyolefin is polypropylene.

6. The process of claim 1 wherein said polyolefin is polyethylene.

7. The process of claim 1 wherein said screen filter has a mesh size of between 20 and 1000 mesh.

8. The process of claim 1 wherein said filtration system is a screen pack comprising at least two filters, wherein one of said filters has a mesh size of greater than 100 and another of said filters has a mesh size of less than 100.

9. The process of claim 1 wherein said articles are selected from the group consisting of fibers and films.

10. A melt extrusion process for making polypropylene fibers, said process comprising:
    a) forming a polypropylene composition comprising a polyolefin resin, and a thermal stabilizing amount of a phosphite of the formula:

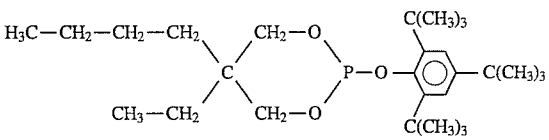

b) melting said composition to form a melted composition,
    c) filtering said melted composition to remove unmelt solids,
    d) passing said filtered composition through a fiber forming die orifice to produce polypropylene fiber.

11. The process of claim 10 wherein said filtering comprises forcing the melted composition through a screen pack comprising at least two screen filters, wherein at least one screen has a mesh size greater than 100 and at least one screen has a mesh size of less than 100.

12. A melt extrusion process for making polypropylene fibers, said process consisting essentially of:
    a) forming a polypropylene composition comprising a polyolefin resin, and a thermal stabilizing amount of a phosphite of the formula:

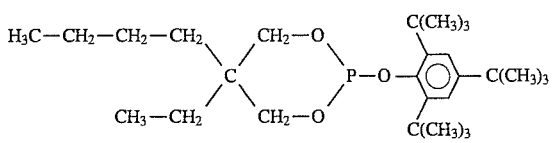

b) melting said composition to form a melted composition,
    c) filtering said melted composition to remove unmelt solids,
    d) passing said filtered composition through a fiber forming die orifice to produce polypropylene fiber.

* * * * *